US012247258B2

(12) United States Patent
Olek et al.

(10) Patent No.: US 12,247,258 B2
(45) Date of Patent: Mar. 11, 2025

(54) EPIGENETIC METHOD TO DETECT AND DISTINGUISH IPEX AND IPEX-LIKE SYNDROMES, IN PARTICULAR IN NEWBORNS

(71) Applicants: Precision for Medicine GmbH, Berlin (DE); The Board of Trustees of the Leland Stanford Junior University, Stanford, CA (US)

(72) Inventors: Sven Olek, Berlin (DE); Rosa Bacchetta, Menlo Park, CA (US)

(73) Assignees: Precision for Medicine GmbH, Berlin (DE); The Board of Truees of the Leland Stanford Junior University, Stanford, CA (US)

( * ) Notice: Subject to any disclaimer, the term of this patent is extended or adjusted under 35 U.S.C. 154(b) by 469 days.

(21) Appl. No.: 17/255,657

(22) PCT Filed: Jul. 3, 2019

(86) PCT No.: PCT/EP2019/067918
§ 371 (c)(1),
(2) Date: Dec. 23, 2020

(87) PCT Pub. No.: WO2020/007951
PCT Pub. Date: Jan. 9, 2020

(65) Prior Publication Data
US 2023/0183804 A1 Jun. 15, 2023

Related U.S. Application Data

(60) Provisional application No. 62/694,149, filed on Jul. 5, 2018.

(51) Int. Cl.
*C12Q 1/68* (2018.01)
*C12Q 1/686* (2018.01)
*C12Q 1/6883* (2018.01)

(52) U.S. Cl.
CPC .......... *C12Q 1/6883* (2013.01); *C12Q 1/686* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS 8,497,066 B2 * 7/2013 Levenson .............. C12Q 1/683
435/6.1
9,926,559 B2 3/2018 Bennett et al.
2016/0024578 A1 * 1/2016 Olek .................... C12Q 1/6851
506/9

FOREIGN PATENT DOCUMENTS

| CN | 101768589 | 7/2010 |
|---|---|---|
| EP | 1826279 A1 | 8/2007 |
| WO | 2010000474 | 1/2010 |
| WO | 2012162660 | 11/2012 |
| WO | 2017203048 | 11/2017 |

OTHER PUBLICATIONS

Barzaghi et al., Journal of Autoimmunity, 2012, 38:49-58 (Year: 2012).*
Barzaghi et al., Frontiers in Immunology, Jul. 2012, vol. 3, Article 211 (Year: 2012).*
Ulirsch et al., 2013, Breast Cancer Res Treat, 137:383-396 (Year: 2013).*
Kleen et al; Journal for Immunotherapy of Cancer; 2015, 3:46, pp. 1-4.*
Sellars et al; Nature Immunology, vol. 16, 2015, pp. 746-755.*
Hejnar et al; PNAS, 98, 2001, pp. 565-569.*
Antequera and Bird, Number of CpG islands and genes in human and mouse, Proc Natl Acad Sci USA, 90: 11995-11999, 1993.
Barbaro et al., Newborn Screening for Severe Primary Immunodeficiency diseases in Sweden—a 2-Year Pilot TREC and KREC Screening Study, J.Clin.Immunol. 37, 51-60 (2017).
Baron et al., DNA demethylation in the human FOXP3 locus discriminates regulatory T cells from activated FOXP3+ conventional T cells, Eur. J. Immunol. 37, 2378-2389 (2007).
Barzaghi et al., Demthylation analysis of the FOXP3 locus shows quantitative defects of regulatory T cells in IPEX-like syndrome, J. Autoimmun. Feb. 2012, 38(1): 49-58.
Boldt et al., Eight-color immunophenotyping of T-, B-, and NK-cell subpopulations for characterization of chronic immunodeficiencies, Cytometry Part B (Clinical Cytometry) 86B: 191-206 (2014).
Booth et al., Quantitative Sequencing of 5-Methylcytosine and 5-Hydroxymethylcytosine at Single-Base Resolution Science, May 18, 2012, vol. 336, No. 6083, pp. 934-937.
Jones and Laird, Cancer Epigenetics Comes of Age, Nature Genetics 21: 163-167, Feb. 1999.
Kristensen and Hansen, PCR-Based Methods for Detecting Single-Locus DNA Methylation Biomarkers in Cancer Diagnostics, Prognostics, and Response to Treatment Clinical Chemistry, 55:8, 1471-1483, 2009.
Laird, The power and the promise of DNA methylation markers, Nature Reviews/Cancer 3:253-266, Apr. 1, 2003.

(Continued)

*Primary Examiner* — Jehanne S Sitton
(74) *Attorney, Agent, or Firm* — BakerHostetler

(57) ABSTRACT

The present invention relates to an epigenetic method for identifying IPEX (immunodysregulation polyendocrinopathy enteropathy X-linked) syndrome and/or IPEX-like syndrome in a human subject using the methylation status of FOXP3 and a control gene specific for a CD4 and/or CD3 T cell. The method is used to distinguish IPEX from IPEX-like and from IPEX-unrelated disorders.

Figure 1:
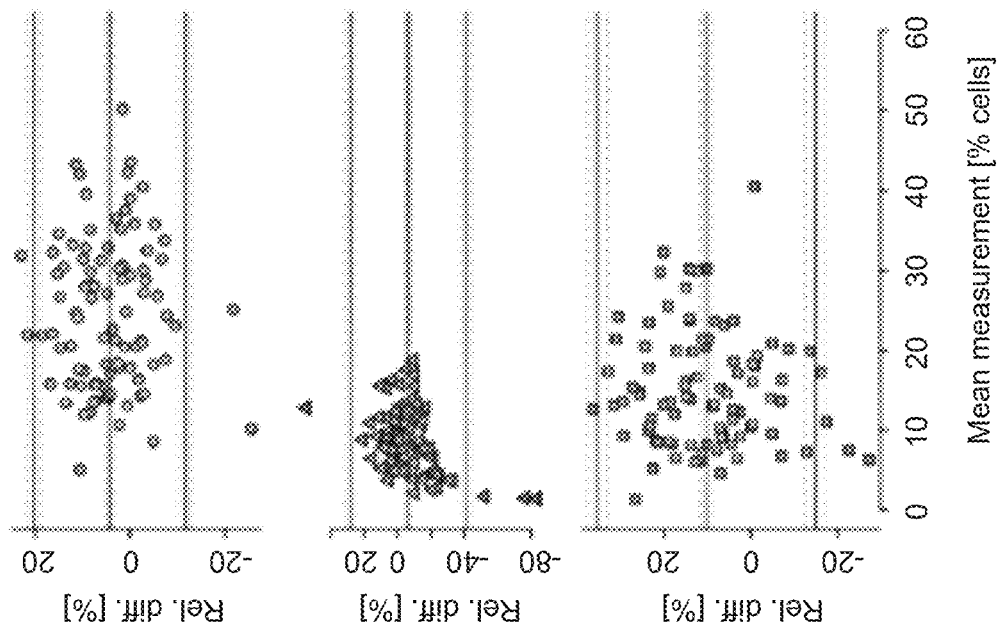
Figure 1:
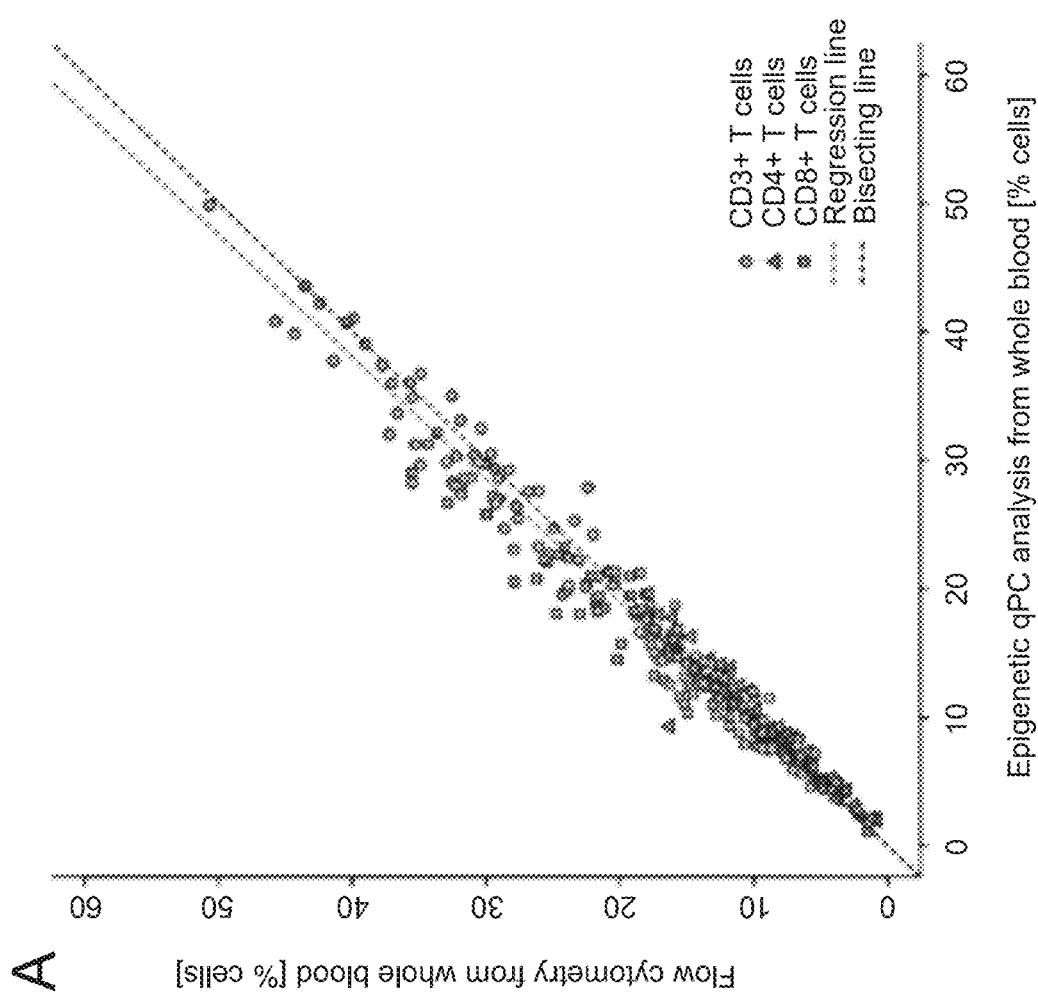
Figure 1:
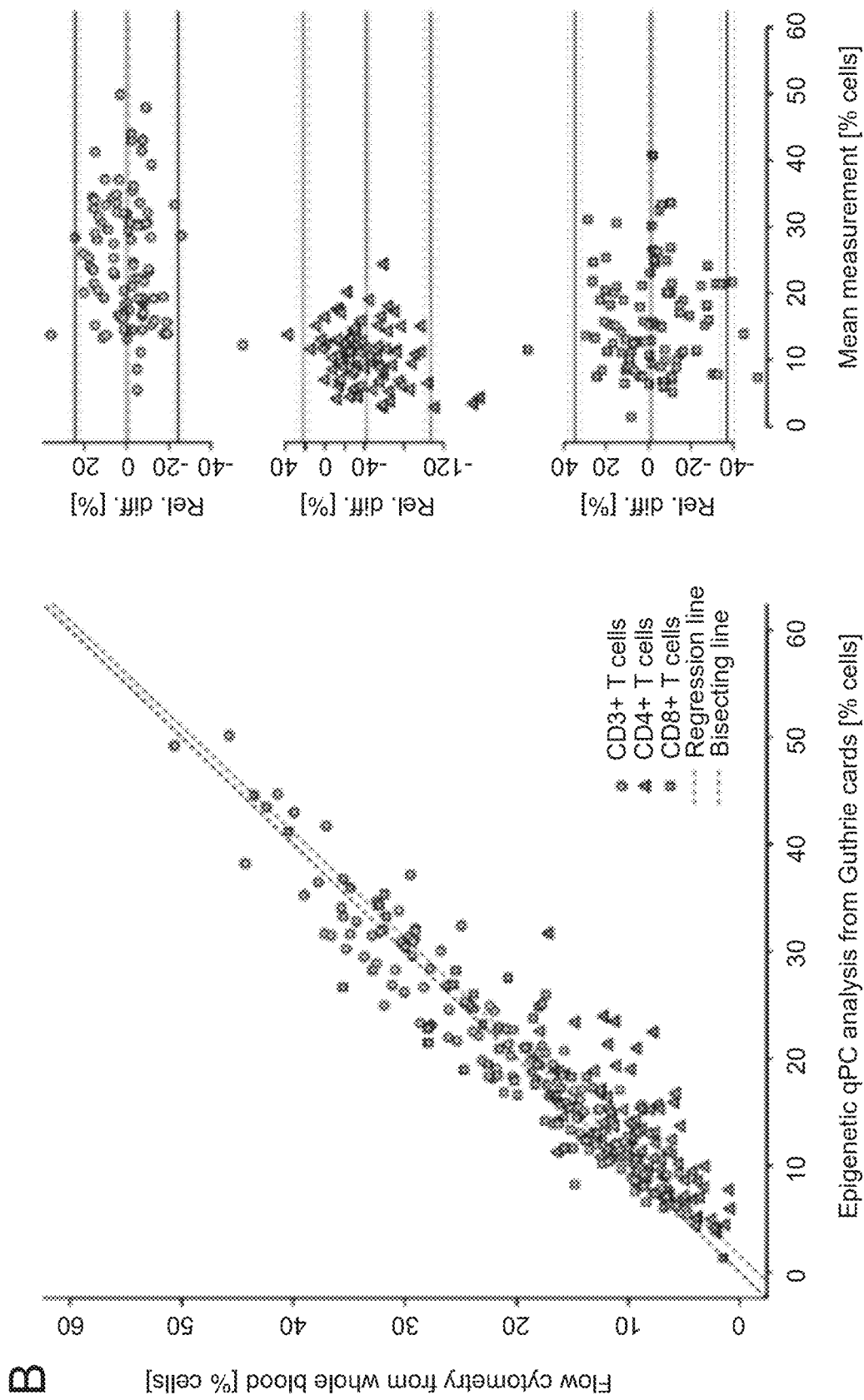
Figure 1:
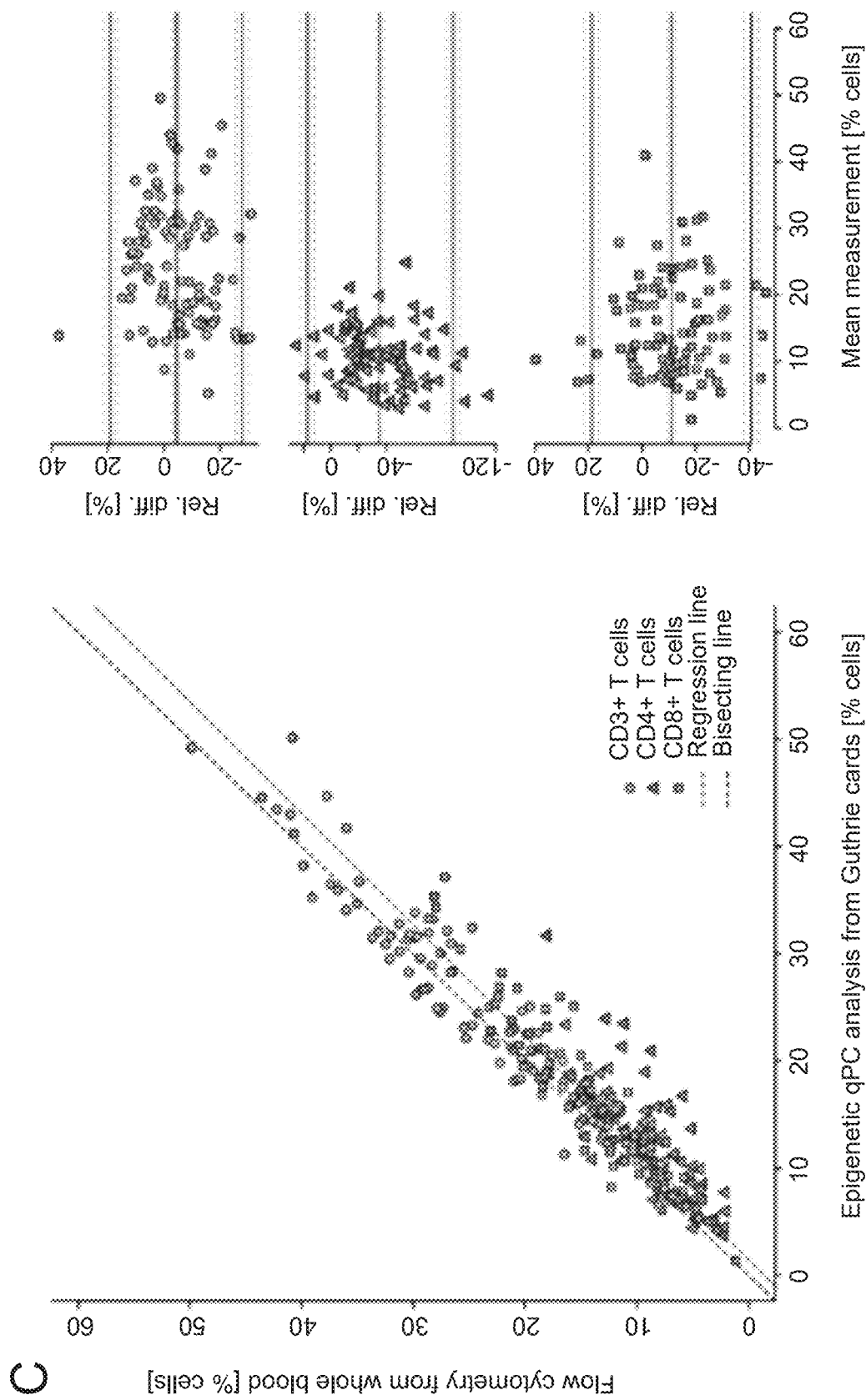

16 Claims, 9 Drawing Sheets
Specification includes a Sequence Listing.

(56) References Cited

OTHER PUBLICATIONS

Williams et al., DNA hypermethylation of CD3(+) T cells from cord blood of infants exposed to intrauterine growth restriction, Diabetologia Aug. 2016, 59: 1714-1723.

Türbachova, Ivana et al., The Cellular Ratio of Immune Tolerance (immunoCRIT) is a Definite Marker for Aggressiveness of Solid Tumors and May Explain Tumor Dissemination Patterns, Epigenetics (2013), vol. 8, Iss. 11, pp. 1226-1235.

* cited by examiner

A

B

SEQUENCE LISTING

<160> NUMBER OF SEQ ID NOS: 13

<210> SEQ ID NO 1
<211> LENGTH: 20
<212> TYPE: DNA
<213> ORGANISM: Homo sapiens

<400> SEQUENCE: 1
tgtttggggg tagaggattt          20

<210> SEQ ID NO 2
<211> LENGTH: 20
<212> TYPE: DNA
<213> ORGANISM: Homo sapiens

<400> SEQUENCE: 2 tatcaccccca cctaaaccaa          20

<210> SEQ ID NO 3
<211> LENGTH: 22
<212> TYPE: DNA
<213> ORGANISM: Homo sapiens

```
<400> SEQUENCE: 3
aaatcctaaa atctcaaaac ca                                              22

<210> SEQ ID NO 4
<211> LENGTH: 21
<212> TYPE: DNA
<213> ORGANISM: Homo sapiens

<400> SEQUENCE: 4
ggtgatgatg gaggtatgtt a                                               21

<210> SEQ ID NO 5
<211> LENGTH: 23
<212> TYPE: DNA
<213> ORGANISM: Homo sapiens

<400> SEQUENCE: 5
atggtggttg gatgtgttgg gtt                                             23

<210> SEQ ID NO 6
<211> LENGTH: 18
<212> TYPE: DNA
<213> ORGANISM: Homo sapiens

<400> SEQUENCE: 6
atggcggtcg gatgcgtc                                                   18

<210> SEQ ID NO 7
<211> LENGTH: 336
<212> TYPE: DNA
<213> ORGANISM: Homo sapiens

<400> SEQUENCE: 7
tgtctggggg tagaggacct agagggccgg gctgggcagc cggcttcctg cactgtctgt     60
tgggacgtcc ctttctgact gggtttctca gaagctgaat gggggatgtt tctgggacac    120
agattatgtt ttcatatcgg ggtctgcatc tgggccctgt tgtcacagcc cccgacttgc    180
ccagattttt ccgccattga cgtcatggcg gccggatgcg ccgggcttca tcgacaccac    240
ggaggaagag aagagggcag ataccccacc ccacaggttt cgttccgaga actggctgcc    300
ctgtcctgca gcaggcttgg cccaggtggg gtgaca                              336

<210> SEQ ID NO 8
<211> LENGTH: 22
<212> TYPE: DNA
<213> ORGANISM: Homo sapiens

<400> SEQUENCE: 8
ggtttttggt attgtaggtt tt                                              22

<210> SEQ ID NO 9
<211> LENGTH: 21
<212> TYPE: DNA
<213> ORGANISM: Homo sapiens

<400> SEQUENCE: 9
ccaattacaa cataacaacc a                                               21

<210> SEQ ID NO 10
<211> LENGTH: 29
<212> TYPE: DNA
<213> ORGANISM: Homo sapiens
```

```
<400> SEQUENCE: 10
tgtttggatg ttgtgtttgt ggtagagtg                                29

<210> SEQ ID NO 11
<211> LENGTH: 22
<212> TYPE: DNA
<213> ORGANISM: Homo sapiens

<400> SEQUENCE: 11
ggttttgtgt atgttaggtt tg                                       22

<210> SEQ ID NO 12
<211> LENGTH: 22
<212> TYPE: DNA
<213> ORGANISM: Homo sapiens

<400> SEQUENCE: 12
ccacattaca acataaacac ac                                       22

<210> SEQ ID NO 13
<211> LENGTH: 29
<212> TYPE: DNA
<213> ORGANISM: Homo sapiens

<400> SEQUENCE: 13
tgttgtgatg ttggttttgg tgtagaggt                                29
```

EPIGENETIC METHOD TO DETECT AND DISTINGUISH IPEX AND IPEX-LIKE SYNDROMES, IN PARTICULAR IN NEWBORNS

CROSS-REFERENCE TO RELATED APPLICATIONS

This application is a 35 U.S.C. § 371 national phase application of International Patent Application No. PCT/EP2019/067918, filed Jul. 3, 2019, which claims the benefit of U.S. Provisional Application No. 62/694,149, filed Jul. 5, 2018, the entire disclosures of each of which are incorporated herein by reference in their entirety.

SEQUENCE LISTING

The Sequence Listing for this application is labeled "113828.000027_Sequence Listing.txt", which was created on Dec. 22, 2020 and is 2 Kilobytes. The entire content is incorporated herein by reference in its entirety.

TECHNICAL FIELD

The present invention relates to an epigenetic method for identifying IPEX (immunodysregulation polyendocrinopathy enteropathy X-linked) syndrome and/or IPEX-like syndrome in a human subject.

BACKGROUND OF THE INVENTION

IPEX (immunodysregulation polyendocrinopathy enteropathy X-linked) syndrome and IPEX-like syndrome are diseases of early childhood that, when untreated, often result in premature death or severe debilitation. Clinically, the diseases present similarly, often indicated by early onset diabetes, eczema and enteropathy. IPEX tends to present with all those—and more—symptoms, whereas IPEX-like can be restricted mainly to enteropathy.

Due to their rare occurrence, both diseases often escape awareness of general, non-immunologist pediatricians. Correct diagnosis then comes late or wrong diagnoses persist, leading to inappropriate treatments falling short of optimal outcome. Permanent damage due to insufficient efficacy of those symptomatic treatments is a likely outcome in both conditions.

IPEX is a disease only known in boys, whereas IPEX-like occurs independent of gender. This distribution is explained by the underlying genetic causes. IPEX results from functional mutations (i.e., non- or missense) in the X-chromosomal FOXP3 gene, coding for a pivotal protein for the formation of functional regulatory T cells (Treg). IPEX-like syndrome instead results from different mutations in autosomal genes involved in the activation and/or development of this same cell type.

In addition to the traditional clinical presentation (i.e., severe enteropathy, type 1 diabetes, and eczema), IPEX may encompass other variable and distinct clinical manifestations. Diagnostic methods for a clear identification of IPEX and IPEX-like are sparse and diagnosis is based on clinical features and on the identification of a pathogenic variant in FOXP3. FOXP3 is the only gene in which pathogenic variants are known to cause IPEX syndrome. As IPEX awareness and characterization have increased, so has identification of FOXP3 mutations, with at least 70 to date. Thus, while FOXP3 is the unifying gene, IPEX is a complex and diverse clinical continuum of disorders.

Despite understanding IPEX pathogenesis, new treatment options have remained elusive, although early diagnosis led to hematopoietic stem cell transplantation (HSCT) and immunosuppression treatment and improved patient outcomes. Also, homeostatic attempts to increase the quantity of Tregs by the body or inducing a higher proliferation of mutated Tregs not intrinsically controlled by the FOXP3 suppressor gene have been proposed.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfate sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

CN101768589 discloses an FOXP3 mutator gene of an IPEX (immunodysregulation polyendocrinopathy enteropathy X-linked syndrome) syndrome major gene. The 68869th-68872th base AAT and the 70207th base T of the internal subregion of the first segment of the mutator gene is in deletion. The mutator gene provides a new theory basis for the pathogenesis of about 30 percent of clinical IPEX syndrome patients and is helpful for clinically developing a screening work of suspected IPEX syndrome patients and the screening work of parents carrying the mutator gene and convenient for fertility guidance and good prenatal and postnatal care. The mutator gene provides a new target spot for the pharmacotherapy of the IPEX syndrome and a theory basis for the research and development of new medicine of the IPEX syndrome. Disclosed is a detection method and a detection kit of the FOXP3 mutator gene.

WO 2017/203048 discloses the use of inosine in the treatment of a disease associated with Treg deficiency or Treg dysfunction, in particular immune dysregulation, polyendocrinopathy, enteropathy, X-linked syndrome (IPEX).

Quantitative abnormalities of lymphoid and myeloid immune cell subsets are indicative for several human diseases and therefore constitute important parameters for diagnosis and patient monitoring. Currently, immune cell quantification is mostly performed by flow cytometry (FCM), which provides flexibility with respect to the analyzed cell types and accuracy. However, although hematology analyzers used in diagnostic laboratories are highly developed and sample logistics are extensively adapted, FCM suffers from intrinsic limitations. FCM-based cell counting requires fresh, anti-coagulated or well-preserved blood samples with intact leukocytes. Even with fresh samples, it is advisable to work quickly since time-to-analysis can influence the results with cell deterioration beginning in the initial hours after blood draw. Time-to-analysis influences results due to cell deterioration within few hours after blood collection. Standardization remains a challenge due to biological, technical and operational variations and standardized protocols remain to be established, especially for samples with low numbers of certain cell populations, e.g. in immunodeficiencies. A critical challenge is that FCM-based cell counting requires intact leukocytes, but fresh or well-preserved blood is not available for all medical applications.

FCM is not applicable in newborn screening for severe, but treatable inborn defects, routinely performed on dried blood spots (DBS). Primary immunodeficiencies (PID) constitute such inborn disease group and are considered or are already part of screening programs. Typically, genetic defects lead to quantitative deficiencies of specific leukocyte subpopulations. Severe combined immunodeficiencies (SCID) represent such PID and are clinically characterized by the absence of T or B cells. Detection of SCID in newborns is currently based on quantitative PCR-assisted T cell receptor (TREC) and immunoglobulin kappa-deleting recombination excision circles (KREC) analyses. These methods reliably detect the lack of recent thymic T cell and bone marrow B cell emigrants, the predominant T and B cell subtypes present in neonatal blood. However, TREC/KREC analysis fails to detect other specific lymphocyte subsets defective in severe PID, such as Natural Killer (NK) cells, regulatory T cells (Treg) or neutrophils. Despite this limitation, TREC newborn screening is effective and shows improved disease outcome due to earlier diagnosis. TREC analysis in newborn analysis is exclusively used for initial screening. Differential diagnosis and patient monitoring prior to and upon the curative hematopoietic stem cell transplantation requires change of technology and is performed by flow cytometry.

In view of the above, it is an object of the present invention to provide an improved and in particular robust method based on DNA-methylation analysis as a superior tool in order to more conveniently and reliably perform newborn screenings for IPEX (immunodysregulation polyendocrinopathy enteropathy X-linked) syndrome and/or IPEX-like syndrome, in particular in routine screenings performed on dried blood spots (DBS).

In one aspect, the present invention solves the above object by providing an epigenetic method for identifying IPEX (immunodysregulation polyendocrinopathy enteropathy X-linked) syndrome and/or IPEX-like syndrome in a human subject, comprising a) providing a blood sample comprising immune cells from said subject, b) analyzing the methylation status of i) at least one CpG position in the human gene region for FOXP3, and analyzing the methylation status of ii) at least one CpG position in at least one human control gene region that is specific for a CD4 and/or CD3 T cells or for all nucleated blood cells, c) determining a ratio of the methylation status as analyzed between i) and ii) in step b), and d) identifying IPEX and/or IPEX-like syndrome in said subject based on said ratio as determined in step c), wherein a value of the methylation status of below a reference range of between about 95% and about 99% is indicative for a non-IPEX-Treg disorder, a value in said reference range is indicative for IPEX-like syndrome, and a value above said reference value is indicative for IPEX.

In the context of the present invention, the diagnostic potential of epigenetic qPCR was demonstrated by identifying PID cases in a cohort of clinically inconspicuous newborns using DBS. It was surprisingly found in the context of the present invention, that patients with IPEX syndrome have high demethylation rates (i.e. above said reference value range, i.e. more than about 99%), and patients with IPEX-like syndrome have lower ones (i.e. below said reference value range, i.e. less than about 95%), and that this can be used as a marker of sufficient specificity/sensitivity to identify and/or detect the diseases.

Barzaghi F et al. (Demethylation analysis of the FOXP3 locus shows quantitative defects of regulatory T cells in IPEX-like syndrome. J Autoimmun. 2012 February; 38(1): 49-58) discloses that TSDR demethylation analysis, alone or normalized for the total T cells, shows that the amount of peripheral Treg cells in a cohort of IPEX-like patients is significantly reduced, as compared to both healthy subjects and unrelated disease controls. This reduction could not be displayed by flow cytometric analysis, showing highly variable percentages of FOXP3(+) and CD25(+)FOXP3(+) T cells. These data provide evidence that a quantitative defect of Treg cells could be considered a common biological hallmark of IPEX-like syndrome. Nevertheless, the IPEX-like in the publication are a mixture of diseases of unknown genetic origin.

To overcome current technological and diagnostic limitations and to broaden applicability of immune monitoring, the inventors established DNA (un-) methylation-based, quantitative assessment of immune cells (epigenetic qPCR). This technique provides relative and absolute immune cell counts applicable to fresh, frozen or paper-spotted, dried blood. Signals are digital, i.e., indicating either one positive or negative value per cell rather than arbitrarily defined thresholds for "positiveness" as in FCM. It can be performed in an automated, operator-independent manner and reduces susceptibility to reagent variability, such as antibodies.

For epigenetic qPCR, genomic DNA is treated with bisulfite. Unmethylated CpG dinucleotides are converted to TpGs, whereas methylated CpGs remain unaltered. Thus, bisulfite conversion translates epigenetic marks into sequence information, allowing discrimination and quantification of both variants. Epigenetic qPCR is non-susceptible to loss of cell integrity since DNA is a stable substrate. It can be performed on fresh-frozen blood, DBS or other specimens without particular demands on preservation state. In addition, PCR components are synthetically produced and standardization is easy to achieve. Nevertheless, immune cell counting via epigenetic qPCR has not yet been demonstrated, due to absence of well-defined specific biomarkers and a lack of definitive and absolute quantification.

Another preferred aspect of the method according to the present invention then relates to the method according to the present invention, further comprising the step of distinguishing between IPEX and/or IPEX-like syndrome in said subject based on said reference value. As mentioned above, if the methylation status of the at least one CpG position in the human gene region for FOXP3 is found at below the reference range of between about 95% and about 99%, this is indicative for a non-IPEX-Treg-related disorder. Then, a value inside said reference range, i.e. of more than 95% demethylation, and less than 99% demethylation is indicative for IPEX-like syndrome, and a value above of said upper reference value of more than 99% ("full" demethylation) is indicative for IPEX.

"About" in the context of the present invention shall mean+/−10% of a given value.

Another aspect of the method according to the present invention then relates to the method according to the present invention, further comprising the step of analyzing the methylation status of at least one CpG position in at least one human gene region where the methylation status is specific for an immune cell selected from a CD3+ T cell, a CD3+/CD4+ T cell, and a CD3+/CD8+ T cell, wherein preferably said gene region is selected from CD3 for a CD3+ immune cell, CD4 for a CD4+ immune cell, and CD8 for a CD8+ immune cell. In general, such human gene regions where the methylation status is specific for an immune cell are known in the art, and can include, for example, T cell specific DNA methylation chip analysis (For example as performed in Williams L et al. DNA hypermethylation of CD3(+) T cells from cord blood of infants exposed to intrauterine growth restriction. Diabetologia. 2016 August; 59(8):1714-23). See also U.S. Pat. No. 9,926,599. In one aspect of the method according to the present invention, more than one gene specific for an immune cell is analyzed, e.g. a panel of 1, 2, 3, 4, 5 or 6 immune cell specific genes is generated as needed or desired, optionally together with more than one demethylation standard gene.

In contrast to flow cytometry, immune cell analysis of Guthrie cards accurately identifies cases PID in newborns. Epigenetic quantification of immune cell populations performs with high equivalence to standard flow cytometry offers a wider range of possible applications, including analysis of dried blood spots allowing also counting of patients in remote areas or from newborns.

At present, neonatal screenings are always performed from DBS. Since FCM is not applicable to this substrate, TREC/KREC analysis is used for PID screening. Introducing epigenetic qPCR in such screening would therefore require equivalence testing to TREC/KREC. Due to different parameters tested, i.e., DNA excision circles vs. genomic DNA, method comparison is not feasible. Instead, the inventors estimated the specificity and sensitivity of TREC/KREC from (43). Epigenetic qPCR reliably identified newborns suffering from different types of PID with similar sensitivity and specificity when using the 99% confidence regions. It only failed to identify one newborn PID patient with maternal cell engraftment, i.e., a patient, where the absence of T and B cells is masked by maternal cells. Unlike the analysis of excision circles, epigenetic analysis is not limited to the main lymphocyte subsets. Such problems may be addressed by expanding the epigenetic qPCR portfolio to markers for memory T or B cells, which are absent in newborns without engraftment. When detected in newborn, such markers may allow detection of engraftment and thereby indicate the absence of a healthy inherent immune system.

Further preferred is the method according to the present invention, further comprising determining the amount of T cells and/or T cell types in said sample based on said methylation status as analyzed, preferably using qPCR, and determining a ratio/ratios of said amount(s). Determination of absolute cell numbers (i.e., cells/µl blood) constitutes the gold standard, e.g. for counting of $CD4^+$ T cells in HIV patients.

This aspect relates to the accurate quantification of methylation data. This involves several components and considerations:

1. An internal standard, e.g. in silico converted plasmids.
2. A (e.g.) GAPDH normalizer in contrast to the methylated variant of a specific gene.
3. Thus, a comparison of all demethylated copies by the obligatory demethylated GAPDH with the specific (but present in the same number of copies) demethylated gene according to the quantification with 1.
4. Nevertheless, the above does not allow a truly "absolute" quantification, since the in silico converted standard does not correspond to the biological sample (which is converted only in the reaction vial.
5. Solving the problem at 4. based on adding and measuring a so-called GNoMs (Genomic Normaliser of Methylation), here, all original sequences are equimolarly included into a plasmid and then submitted to the overall process (bisulfite treatment and purification). Since they are present 1:1 a standard can be identified after the quantification using the standards in 1 showing the difference between in silico and in situ methylation. Using this factor, the methylation value of the measurements can be corrected, which improves the result considerably.
6. Using a defined amount of a nucleic acid (plasmid) with a standard gene having inverted CG bases, furthermore, any loss of material during the process can be accounted for, which further improves the method.
7. Reliable and specific assay components designed for clinical practice and needs.

In this aspect of the method, the amplification is normalized using a first in silico bisulfite converted nucleic acid (plasmid), comprising a demethylation standard gene (e.g. GAPDH), an "artificial sequence" (the sequence inversing all CpG dinucleotides to GpC), as well as a blood cell specific gene (a "specific gene", e.g. CD4). All three elements are equally present (equimolar) on said nucleic acid, and are in silico bisulfite converted. Therefore, the normalization curve and the corresponding calibration curves can be directly compared with the sample, and the relative cell count can be determined from the ratio of blood cell specific gene to demethylation standard gene. Nevertheless, the nucleic acid does not correspond to the "real" sequence, since each C is replaced by a T. A serial dilution and determination of each concentration with all genes as mentioned generated the calibration curve for the assay. Preferably, the nucleic acids are plasmids, e.g. linearized plasmids, such as bacterial plasmids, e.g. pUC, a yeast artificial chromosome (YAC), human artificial chromosome (HAC), PI-derived artificial chromosome (PAC), a bacterial artificial chromosome (BAC), and/or a PCR-product.

In order to improve the accuracy of the approach, a second nucleic acid (plasmid) is used comprising the demethylation standard gene (e.g. GAPDH), the "artificial sequence" (the sequence inversing all CpG dinucleotides to GpC), and the blood cell specific gene (a "specific gene"). Nevertheless, these sequences are NOT in silico bisulfite converted, and correspond to the genomic sequences (in as far as the have a genomic counterpart, see below)—and thus can only be used for measuring the amplification (e.g. qPCR) efficiency.

The reason for the second standard is two-fold. A) For a definitive quantification a standard is required that is identical as in the biological sample to be analyzed (this is also a regulatory requirement). In the first nucleic acid, nevertheless, a double stranded AT-rich sequence is compared with a single-stranded U-rich sequence. Only the "true" bisulfite conversion of the double stranded nucleic acid allows for this definitive comparison. Then, the quotient of bisulfite conversion of blood cell specific gene to demethylation standard gene, normalized using the first nucleic acid, gives a factor of the efficiency. The same holds true for a quotient based on the division of the bisulfite conversion of the sequence inversing all CpG dinucleotides to GpC by the bisulfite conversion of the demethylation standard gene.

Preferably, the "artificial sequence" (the sequence inversing all CpG dinucleotides to GpC) is a random sequence comprising C and CpG sequences (for bisulfite conversion) that does not occur in the human genome. In one embodiment, the artificial sequence is the exact sequence of the part of GAPDH that is amplified (amplicon) wherein the CpG sequences are inverted into GpC sequences. The "artificial sequence" is found on all three nucleic acids as described above, namely on the first one (in silico bisulfite converted), the second one (for bisulfite conversion), and—as the only analyzed sequence—on the third nucleic acid (in silico bisulfite converted).

The third nucleic acid is given in a defined amount into a defined amount of blood, in particular from a newborn, and is then analyzed (e.g. purification, bisulfite treatment, second purification, desulfonation, specific amplification). Then, a normalization is performed against the first nucleic acid (how many copies were measured and given into the reaction), the efficiency is determined using a comparison with the second nucleic acid, and the (residual) copy number is determined using the third nucleic acid. Any losses are compared with a loss of genomic DNA that was subjected to the same procedure. The overall process allows for a precise definitive and absolute quantification of said DNA, and through this the cells in a blood sample, such as, for example, whole blood.

In one embodiment, the invention relates to an artificial sequence that is the exact sequence of the part of GAPDH that is amplified (amplicon) wherein the CpG sequences are inverted into GpC sequences as a tool when performing the method(s) of the present invention.

The composition of the cellular immune system holds valuable diagnostic information for various diseases. The standard technology for quantitative immune cell monitoring is flow cytometry. However, this method is limited to blood samples in which cell-integrity is retained. In clinical routine, this effectively restricts analysis to fresh blood samples as analytical substrate.

Thus, in a preferred embodiment of the method according to the present invention, said at least one CpG position is present in the 5' region upstream from the transcription start, promoter region, the 5' or 3' untranslated regions, exon, intron, exon/intron border and/or in the 3' region downstream of the transcriptional stop of said gene region as analyzed.

Preferred is the method according to the present invention, wherein the methylation status of at least one CpG position in the Treg-specific demethylated region (TSDR) in FOXP3 is analyzed. The Treg-specific demethylated region (TSDR) according to SEQ ID NO. 7 and its analysis has been described previously (WO 2010/000474, DNA methylation analysis of regulatory t cells through DNA-methylation analysis of the tsdr region of the gene foxp3, herewith incorporate by reference in its entirety). Said analysis of the methylation status comprises amplification with at least one primer of the primer pairs selected from SEQ ID No. 1 and 2 and SEQ ID No. SEQ ID No. 3 and 4, and said analysis of the methylation status preferably comprises analyzing the methylation status of at least one CpG position as analyzed by any of the probes according to SEQ ID Nos 5 to 6.

Preferred is the method according to the present invention, wherein said human control gene region that is unspecific for a T cell type is selected from a housekeeping gene, such as, for example, beta-2microglobulin (B2M), peptidyl-prolyl isomerase A (PPIA), eukaryotic translation elongation factor 1 gamma (EEF1G), succinate dehydrogenase complex subunit A (SDHA), glyceraldehyde 3-phosphate dehydrogenase (GAPDH), hydroxymethyl-bilane synthase (HMBS), TATA box-binding protein (TBP), 18s Ribosomal RNA (18sRNA), phosphoglycerate kinase 1 (PGK1), and beta-actin (BACT).

In order to analyze the methylation status (also known as bisulfite convertibility) of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature. In a preferred embodiment of the method according to the present invention, said method is suitable for routine application, for example on a DNA-chip. Based on the above information and the respective literature, the person of skill will be able to adjust the method as above to such settings. In a preferred embodiment of the method according to the present invention, said analysis of bisulfite convertibility comprises amplification with at least one primer of suitable primer pairs that can be suitably designed based on SEQ ID No. 7, preferably oligomers according to any of SEQ ID No. 1 through 6.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethyLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)). With the amplification, the amplicon of the CD4 gene or any paralog or ortholog as described herein is produced that is a particularly preferred "tool" for performing the method(s) according to the present invention.

The person of skill will furthermore be able to select specific subsets of CpG positions in order to minimize the amount of sites to be analyzed, for example at least one of CpG position 1, 2, 3, 4, 5, and 6 of the TSDR, or all sites as present on the TSDR. The positions are numerically counted from the 5'-end of an amplicon as generated and analyzed. Preferred are combinations of 4, 5, 6, or 7 positions, which are producing enough information in order to be informative in the context of the present invention.

Preferred is the method according to the present invention, further comprising the step of mutational analysis of the gene for FOXP3 in said subject. IPEX is a disease only known in boys, whereas IPEX-like occurs independent of gender. This distribution is explained by the underlying genetic causes. IPEX results from functional mutations (i.e., non- or missense) in the X-chromosomal FOXP3 gene, coding for a pivotal protein for the formation of functional regulatory T cells (Treg). IPEX-like syndrome instead results from different mutations in autosomal genes involved in the activation and/or development of this same cell type. FOXP3 is the only gene in which pathogenic variants are known to cause IPEX syndrome. As IPEX awareness and characterization have increased, so has identification of FOXP3 mutations, with at least 70 to date. Thus, while FOXP3 is the unifying gene, IPEX is a complex and diverse clinical continuum of disorders.

Preferred is the method according to the present invention, wherein said sample is selected from a fresh blood sample, a peripheral or capillary blood sample, a sample of blood lymphocytes or a fraction thereof, a tissue sample, a previously frozen blood or tissue sample, and a dried blood sample (DBS), such as a Guthrie card.

Also preferred is the method according to the present invention, comprising the step of diagnosing primary immunodeficiencies (PID) in a human, in particular a newborn, based on said quantification, wherein said sample preferably is a dried sample, like a Guthrie card (see also further below).

Preferred is a method according to the present invention, further comprising the step of concluding on the immune status of a mammal based on said quantification.

Preferred is the method according to the present invention, wherein said human subject is selected from a fetus, a newborn, and a child.

The present invention also encompasses a method for an improved treatment of IPEX syndrome and/or IPEX-like syndrome in a human subject, in particular a newborn, in need thereof, comprising performing the method as described herein on a sample taken from said human subject and providing a specific treatment for IPEX syndrome or IPEX-like syndrome depending on said on said identifying.

One additional embodiment comprises a method for monitoring the treatment of IPEX syndrome and/or IPEX-like syndrome in a human subject, comprising performing the method as described herein on a sample taken from a human subject that is treated for IPEX syndrome and/or IPEX-like syndrome, and comparing said ratio(s) as identified to the ratio(s) in a sample taken earlier or in parallel from the same human, and/or to a control sample, and concluding on said treatment based on said comparing.

Another aspect of the invention relates to a kit for identifying, and/or monitoring IPEX syndrome and/or IPEX-like syndrome in a human subject, comprising components for performing a method according to the present invention, in particular a kit comprising a) a bisulfite reagent, and b) materials for the analysis of the methylation status of CpG positions in the region of FoxP3, preferably the TSDR, and GAPDH. The kit optionally comprises instructions for use. The diagnostic kit particularly contains oligonucleotides (e.g. for producing amplicons) specific for regions of interest, bisulfite reagents, and/or components for PCR. The diagnostic kit and its use encompasses but is not limited to the diagnosis of a disease and/or the follow-up of a disease and/or the predisposition and/or the assessment of a risk for IPEX syndrome and/or IPEX-like syndrome and/or the monitoring of an effect of a chemical or biological substance (drug) on said IPEX syndrome and/or IPEX-like syndrome.

Another aspect of the invention relates to the use of the kit according to the invention for performing a method according to the invention, i.e. for identifying, and/or monitoring IPEX syndrome and/or IPEX-like syndrome in a human subject.

The inventors implemented epigenetic qPCR systems for quantification of the major leukocyte populations. Upon determining immune cell type specific methylation marks, whole blood from 25 healthy donors, and 325 Guthrie cards from newborns including 25 cards from patients with primary immunodeficiencies (PID) were analyzed. Methodological concordance between flow cytometric and epigenetic data for B-, NK-, total T cells, T helper cells and cytotoxic T cells was determined and the ability of this new technique to identify quantitative immune cell deficiencies was challenged.

For DBS, where the blood volume is difficult to define, copies of unmethylated immune cell-type specific marker genes were related to copies of a human control gene region that is unspecific for a T cell type is selected from a housekeeping gene such as the universal denominator GAPDH. For simultaneous quantification of different cell types in biological samples, the inventors then designed a calibrator plasmid containing the unmethylated genomic sequences of GAPDH as reference quantifier and the cell type-specific markers. The GAPDH locus selected here is stably diploid and always unmethylated. Therefore, through adjusting the quantification of biological samples with the in silico bisulfite-converted standard and by the calibrator, assay specific technical inefficiencies can be corrected and allows definitive quantification of the respective loci relative to unmethylated GAPDH, i.e., all nucleated cells.

As such, epigenetic qPCR displays a direct proportional relation to cell types as determined by FCM. The data suggest that epigenetic qPCR, both from liquid and dried blood substrates, performs equivalent to FCM for the relative quantification of immune cells.

Further quantitative defects of other immune cell populations occur in highly specialized Tregs. The inventors' data indicate that identification of such patients based on epigenetic qPCR for Tregs is possible early after birth, allowing for early diagnosis of IPEX, which constitutes a potentially life-threatening PID. Moreover, the ability to quantify Tregs opens the door to the early diagnosis of IPEX-like diseases recently described as Treg-deficiencies due to genetic mutations of different genes (e.g. IL2RA, STAT5b, and ITCH). Epigenetic qPCR provides an option in medical screening procedures, and epigenetic qPCR provides precise and accurate means for immune monitoring and it underscores that epigenetic qPCR can assist current immune diagnostics, in particular for DBS.

The invention will now be further described based on the following examples and with reference to the accompanying figures and the sequence listing, without being limited thereto. For the purposes of the present invention, all references as cited herein are incorporated by reference in their entireties.

FIG. 1 shows the epigenetic qPCR of neonatal DBS. Copies from cell-type specific qPCRs (y-axis) plotted against GAPDH copies (x-axis). (A) unmethylated CD3G/D, B) MVD and C) LRP5. DBS from healthy neonates (n=250, grey circles) estimate reference ranges for each assay as defined by 99% confidence region (red ellipse) and 99.9% confidence region (blue). 24 DBS from PID-diagnosed newborns are shown as colored circles, each referencing disease characteristics shown in Table 1.

Figure 2:
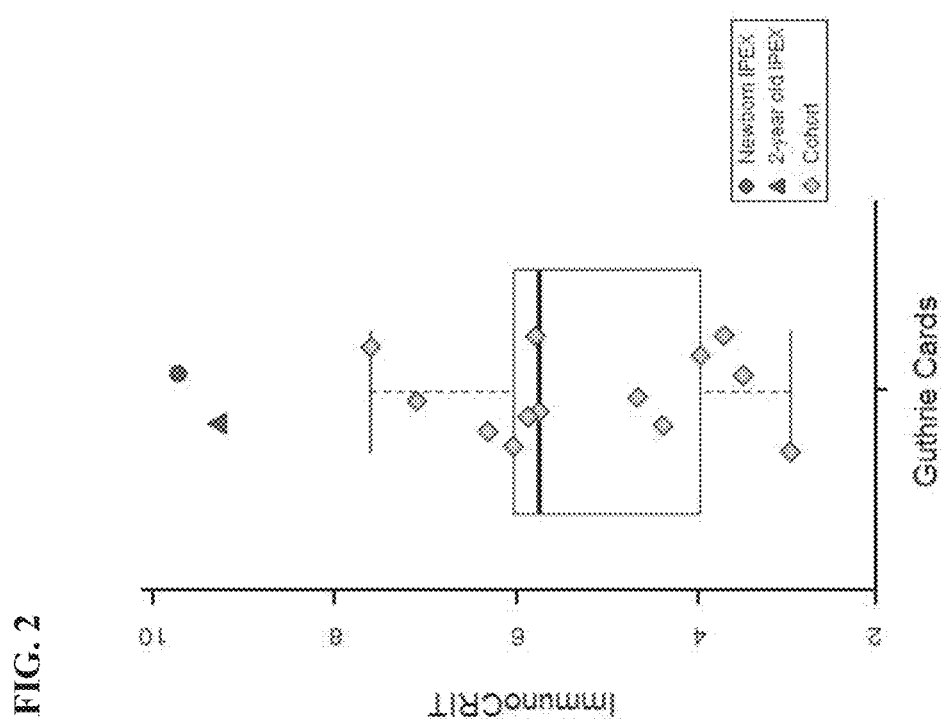

FIG. 2 shows the epigenetic qPCR on DBS from newborns with SCN or IPEX. DBS from healthy controls (grey+box) and newborns with IPEX were subjected to epigenetic qPCR for quantification of Treg/CD3 ratio (ImmunoCRIT) depicted in. Healthy cohorts are represented in the boxplot and results from diseased patients are depicted in red.

Figure 3:
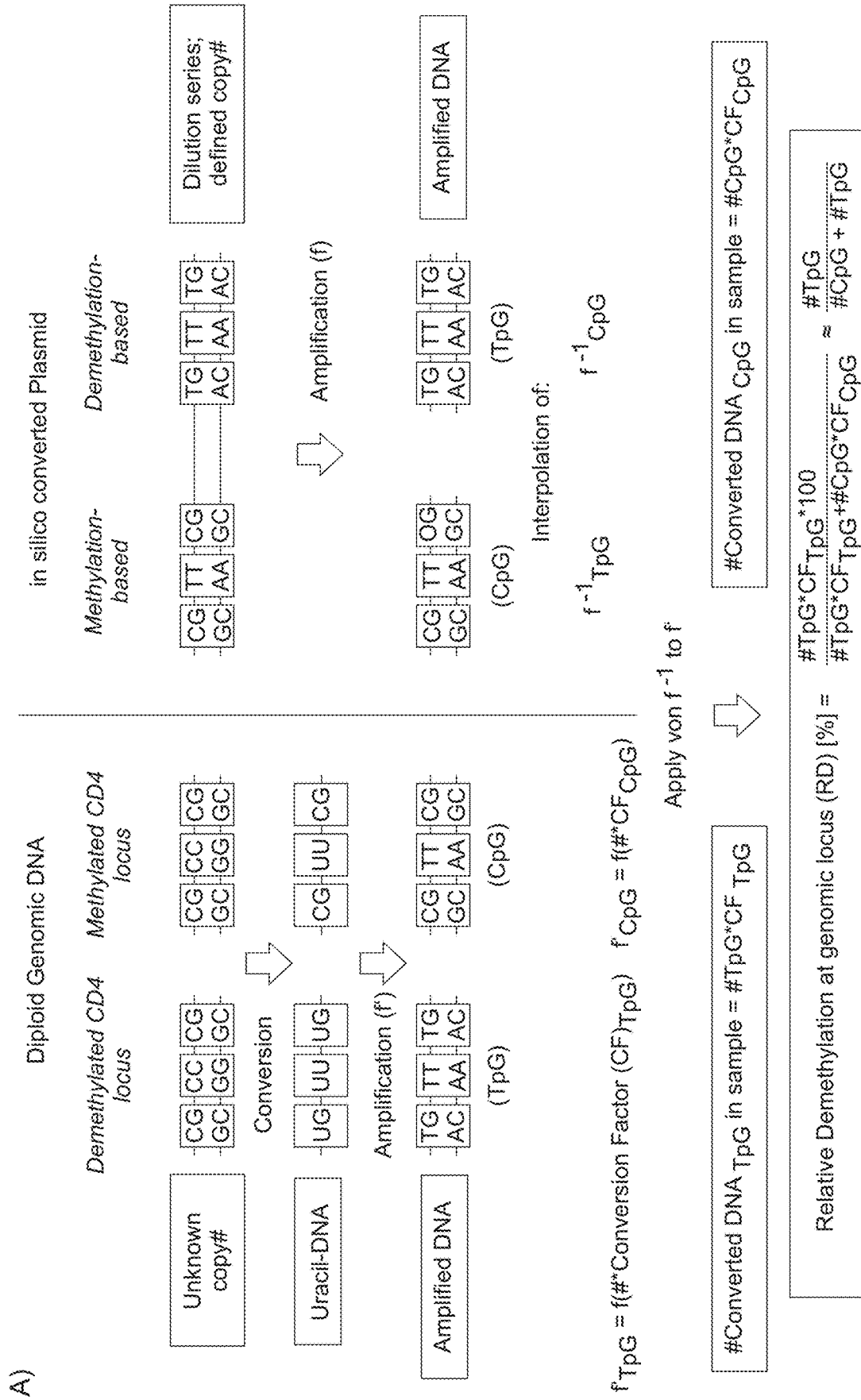
Figure 3:
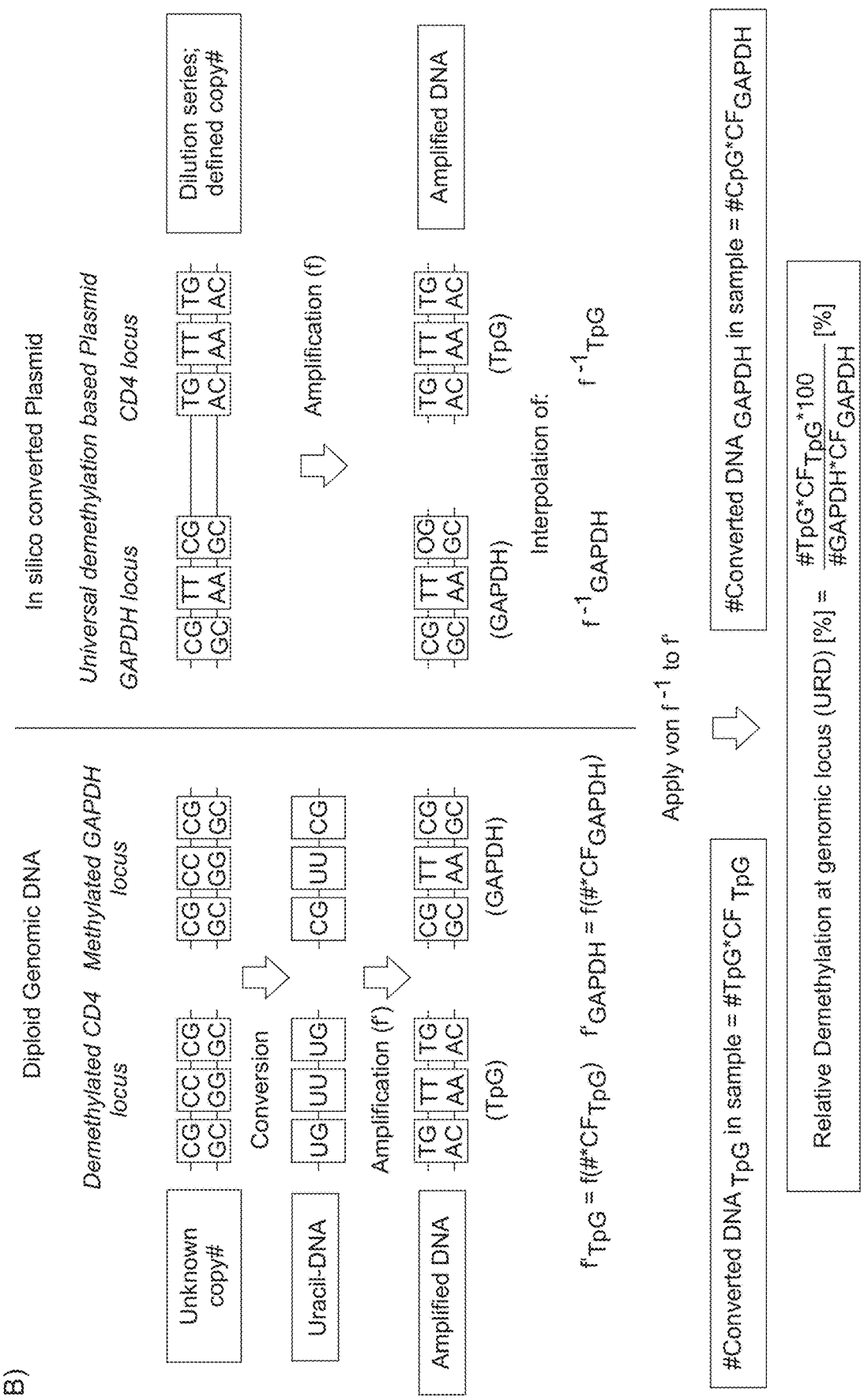
Figure 3:
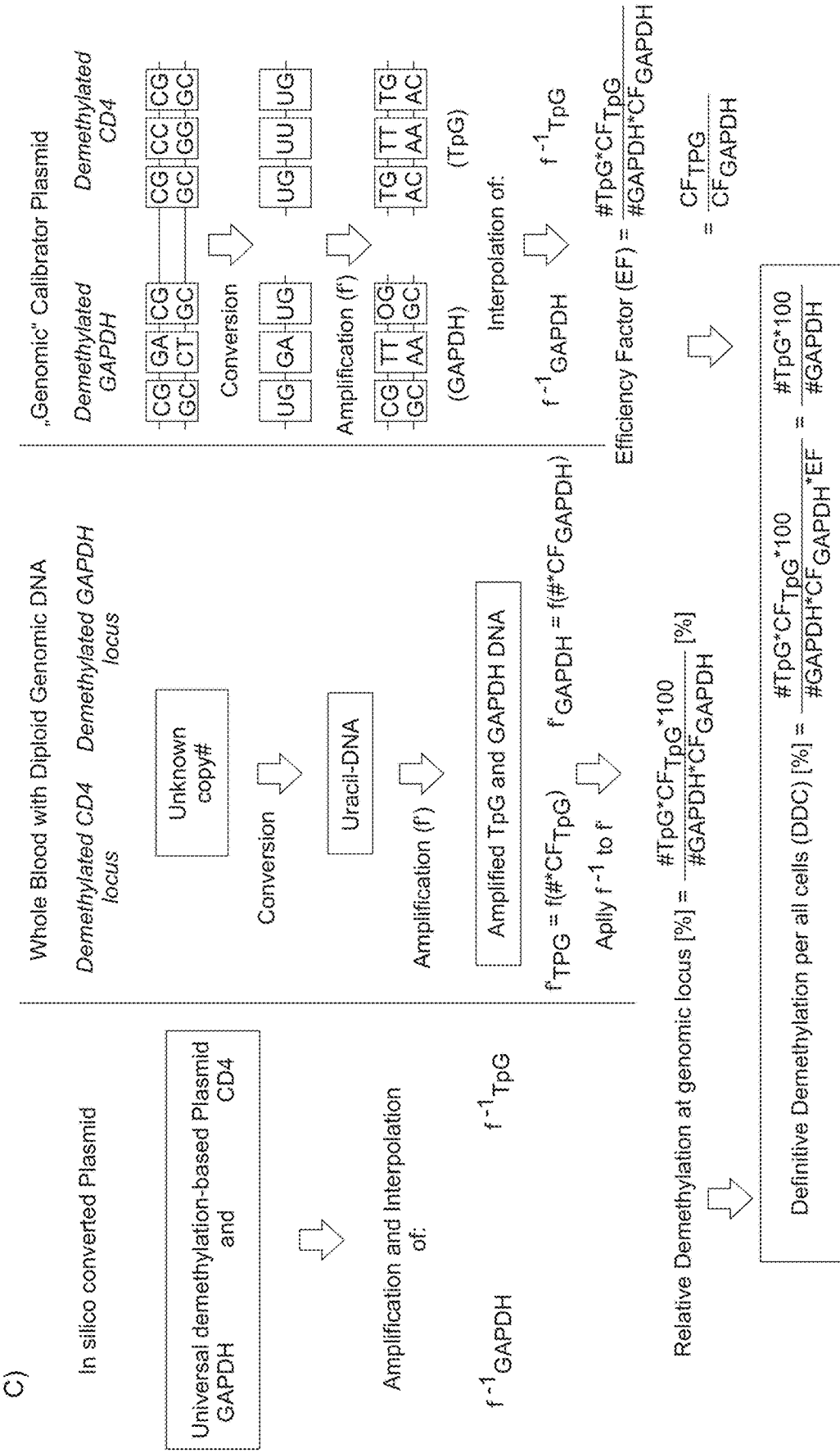
Figure 3:
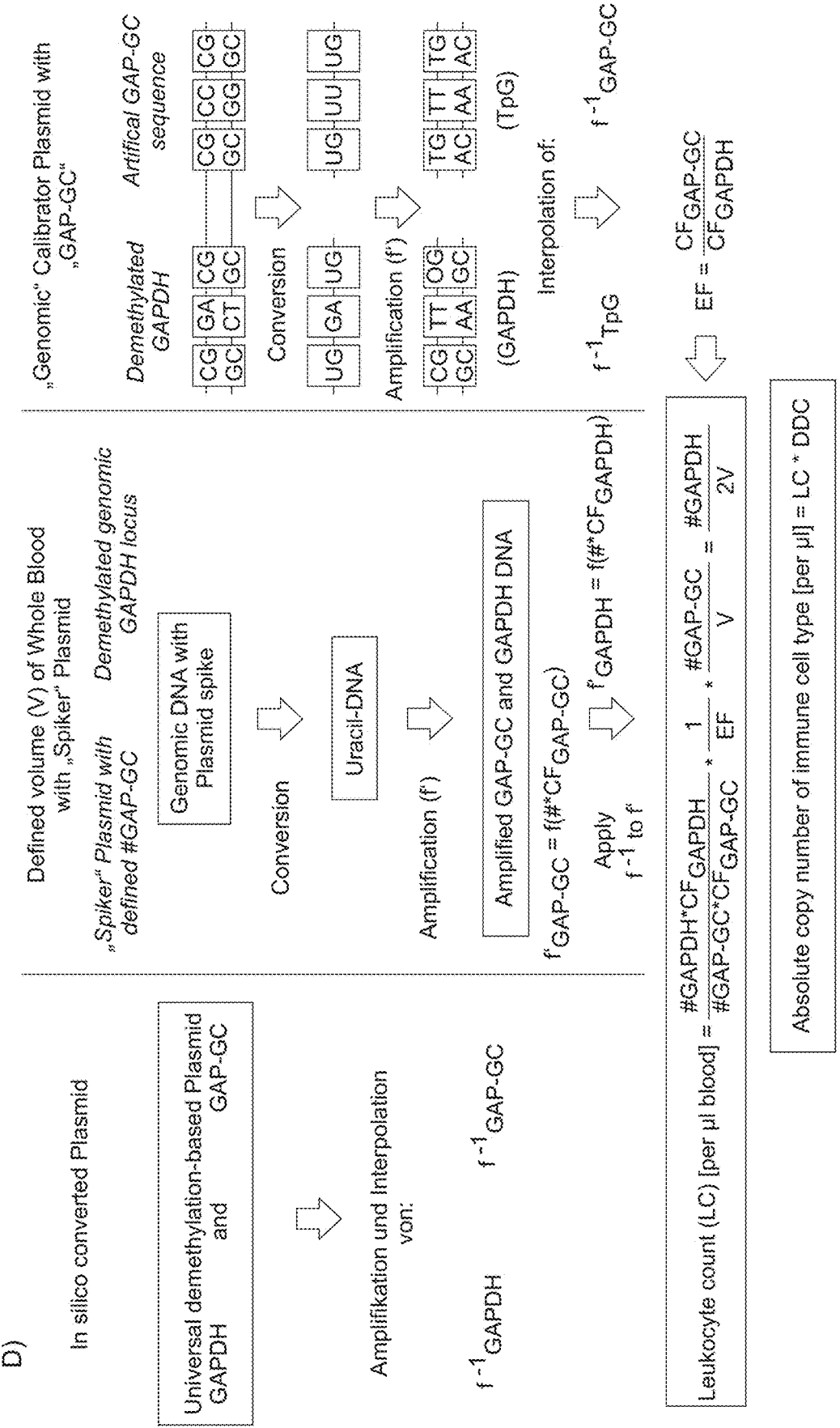

FIG. 3 shows a schematic overview over the different quantification approaches for epigenetic cell counting. In A) locus-specific relative percentage quantification is illustrated. qPCRs allow counting of copy numbers as based on the calculation of serially diluted in silico converted plasmids by a linear interpolation (f-1) of the amplification results (f). Relative percentage methylation at the genomic locus is calculated by the interpolated copy number of originally unmethylated copies at this locus divided by all copies at this locus, i.e., the methylated and unmethylated ones. Conversion in the biological sample perturbs the integrity of the genomic DNA, whereas the plasmid represents the amplification product and not the substrate. The resulting difference in amplification efficiency is given by an unknown "conversion factor, (CF)". It is considered negligible when comparing amplification of two highly homologous sequences with few methylation-status dependent SNPs. In (B) the universally unmethylated GAPDH locus (representing the total number of genomic DNA copies) is used as denominator to determine the ratio of any cell-type specifically unmethylated locus. Here, CF leads to substantial shifts between the different qPCR assays. In C) a calibrator plasmid containing equimolar genomic target sequences is used to compensate for conversion efficiencies at the different genomic loci introducing the efficiency factor (EF). D) For counting absolute numbers of cells in a defined volume of blood, a known copy number of plasmid containing a synthetic, not natural DNA sequence (GAP-GC) is supplemented. Interpolating the starting amount of GAP-GC allows monitoring of DNA preparation, conversion and qPCR providing a good estimator for process efficacy.

Figure 4:
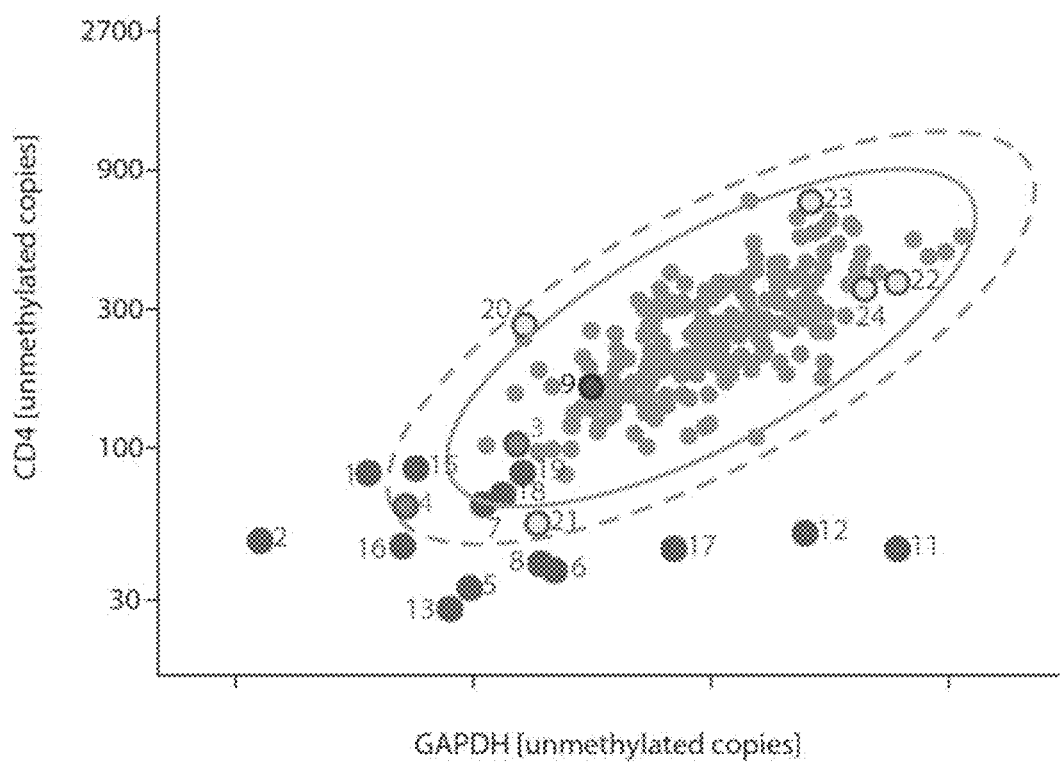
Figure 4:
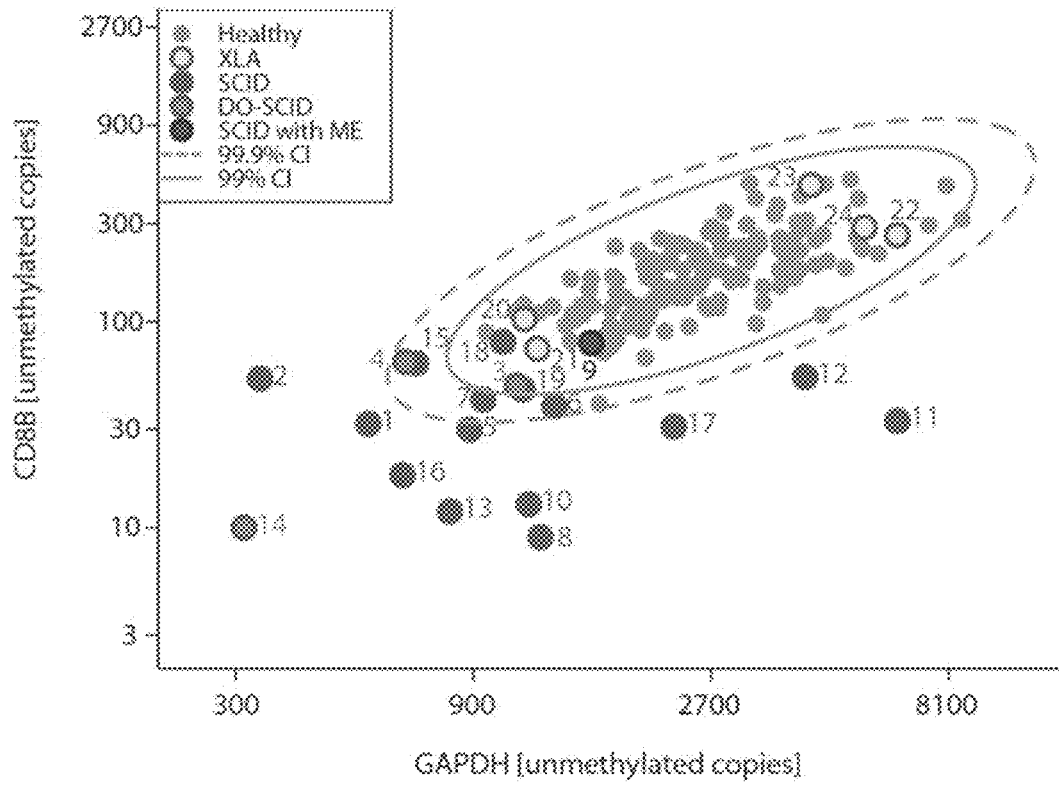

FIG. 4 shows epigenetic immune cell quantification on DBS from newborns. Dried blood spots on Guthrie cards were subjected to epigenetic qPCR analysis for the quantification of unmethylated CD4 (A; specific for $CD4^+$ T cells) and CD8B (B, specific for $CD8B^+$ T cells) gene copies. Calculated values from the immune cell specific assays (y-axis) were scatter plotted over parallel measured GAPDH copies (x-axis). Reference samples from healthy neonates (n=250, grey dots) were measured and used to estimate normal ranges for each assay as defined by red (99% confidence region) and azure (99.9% confidence region) ellipses, respectively. 24 samples from newborns each with a diagnosed PID (classification as indicated in the legend box at the lower right) are shown as red, blue, green and black circles, each associated with an identifier referencing disease characteristics according to table 1.

SEQ ID NO: 7 shows the nucleotide sequence of the human FoxP3 TSDR.

EXAMPLES

Study Design—The research objective was to determine if epigenetic qPCR can complement current methods for diagnostic immune cell counting. To test this, the inventors identified and evaluated cell-type specifically unmethylated DNA loci, for Tregs. Epigenetic qPCR was developed and standardized using established normalization parameter. Critical steps for this normalization were to provide for comparable measurement for all cell-specific qPCRs by adjusting for qPCR efficiency between different genomic loci and different bisulfite conversion effects of different regions as well as normalization for DNA purification efficiency for absolute quantification of cells per blood volume. Both, relative and absolute quantification was applied to evaluate whole blood from 25 healthy donors as well as dried spots from 250 dried blood spots from healthy newborn and 24 newborns cards from newborn patients with primary immunodeficiencies. Results of epigenetic qPCR were verified for equivalence to standard FCM and furthermore tested in applications with current diagnostic undersupply in immune cell counting, in particular primary and acquired immune deficiencies. Patient material was provided from German and Californian hospitals and blinded prior to data analysis.

Dried blood spots—Three 3.2 mm DBS punches of genetically confirmed IPEX patients, from 250 randomly selected anonymous newborns and from capillary blood of one patient with confirmed IPEX were obtained. The sequencing and genetic confirmation of the included PID patients was performed in compliance with the practitioner toolkit of the Clinical Sequencing Exploratory Research (CSER) Consortium. Written parental consent was obtained for all participants. The study was approved by the Medical Association Chamber of Saxony ethics committee or institutional review board at University of Freiburg, Germany.

Peripheral whole blood—EDTA-anticoagulated peripheral blood was collected from 25 healthy subjects at Leipzig University with ethical consent. Samples were subjected to epigenetic qPCR and to standard FCM. Information was blinded to experimenters.

DNA preparation and bisulfite conversion—For purified cells, genomic DNA was isolated and bisulfite treated using DNeasy tissue and EpiTect Fast Bisulfite conversion kits (Qiagen, Hilden, Germany) according to the manufacturer's instructions. For EDTA-blood, 20 µl substrate was supplemented with 16 µl lysis buffer, 3 µl proteinase K (30 mg/mL) and GAP[GC] plasmid (final concentration 20,000 copies/µl) and lysed for 10 minutes at 56° C. For conversion, EpiTect Fast Bisulfite Conversion Kit was used. 3×3.2 mm DBS punches were added to 68.75 µl lysis buffer, 10.75 µl proteinase K (30 mg/mL), 20,000 copies/µl GAP[GC] plasmid (final concentration) and lysed for 60 minutes at 56° C. Conversion was performed for 45 min at 80° C. adding 180 µl ammonium bisulfite (68%-72%, pH 4.8-5.3, Chemos AG, Munich, Germany) and 60 µl tetrahydrofuryl alcohol (Sigma-Aldrich). For purification "My Silane Genomic DNA kit" (Invitrogen, Carlsbad, CA) was used following manufacturer's instructions. Bisulfite conversion rates were analyzed previously and are provided in the manufacturer's manual with values above 98% (49). Efficiency of conversion was routinely checked by bisulfite sequencing showing rates above 98%. As process control, the genomic calibrator included conversion controls in each individual qPCR. BioPerl was used for in silico bisulfite conversion of sequences (50).

Epigenetic qPCR—Thermal cycling was done as follows: 1×95° C. for 10 or 35 min followed by 50×95° C. for 15 sec, and 61° C. for 1 min in 5 µl (DBS) or 10 µl (EDTA-blood) using Roche LightCycler 480 Probes Master. For calculation of cell numbers from autosomal genes, a 2:1 allele-to-cell ratio was assumed. For $RD_{ls}$ [%], TpG-copies were divided by TpG-+CpG-copies. For $RD_u$ [%], the quotient of TpG copies (of the respective immune cell type) and GAPDH copies was calculated. For $DD_u$ [%], $RD_u$ were corrected by EF compensating for performance differences between different qPCRs. For assay-specific EF, the inventors used a plasmid-based calibrator harboring the genomic target region of all qPCRs, including GAPDH (universal denominator) and an artificial GAP[GC] region. The calibrator was subjected to bisulfite conversion followed by qPCR. EF was calculated by dividing measured TpG copies by parallelly measured GAPDH copies. EFs were derived from approximately 25 experiments. For absolute quantification, an artificial GAPDH sequence inversing all CpG dinucleotides to GpC (GAP[GC]) and its corresponding epigenetic qPCR were designed without cross reactivity with endogenous GAPDH. EF for GAP[GC] was 0.87 with an 95% CI of 0.75-1.00.

Combined TREC/KREC newborn screening assay—TREC/KREC screening was applied as described previously (M. Barbaro, et al., Newborn Screening for Severe Primary Immunodeficiency Diseases in Sweden—a 2-Year Pilot TREC and KREC Screening Study, *J. Clin. Immunol.* 37, 51-60 (2017)). Briefly, DNA from one 3.2-mm punch of the original DBS was extracted in a 96-well format, and quantitative triplex real-time qPCR for TREC, KREC, and β-actin (ACTB) was performed using a ViiA7 Real-Time PCR System (Applied Biosystems, Foster City, CA, USA). TREC and KREC copy numbers were determined per 3.2-mm punch. ACTB was used to verify suitable DNA amounts per DBS and not for normalizing TREC/KREC copies.

Plasmids—Sequences, corresponding to methylated or unmethylated, bisulfite-converted genomic regions, were designed in silico and inserted into plasmid pUC57 (Genscript Inc., Hongkong, China) and used for assay establishment and as qPCR quantification standard. Standard plasmids harbor all assay target sequences equimolarly. Plasmids were spectrophotometrically quantified, linearized by ScaI and serially diluted in 10 ng/µl of λ-phage DNA (New England Biolabs) to obtain 31250, 6250, 1250, 250, 50 or 30 copies in the final reaction. Calibrator plasmid harbors all assay target sequences equimolarly in genomic unconverted, unmethylated version. Artificial spike-in plasmid carries unconverted GAPDH with inverted CpG dinucleotides (GAP[GC]).

Oligonucleotides—Oligonucleotides (Metabion AG, Munich, Germany) are as follows:

| Oligonucleotides for qPCR analysis | | | | |
|---|---|---|---|---|
| Gene | Assay variant | Sequence (5'-3') | SEQ ID No. | Conc. [µM] |
| FOX | Fw. | TGTTTGGGGGTAGAGGATTT | 1 | |
| | Rev. | TATCACCCCACCTAAACCAA | 2 | |
| | Fw. | AAATCCTAAAATCTCAAAACCA | 3 | |
| | Rev. | GGTGATGATGGAGGTATGTTA | 4 | |
| | Probe | non-methylated ATGGTGGTTGGATGTGTTGGGTT | 5 | |
| | | methylated ATGGCGGTCGGATGCGTC | 6 | |
| GAPDH | TpG | | | |
| | Fw. | GGTTTTTGGTATTGTAGGTTTT | 8 | 1.5 |
| | Rev. | CCAATTACAACATAACAACCA | 9 | 1.5 |
| | Probe | TGTTTGGATGTTGTGTTTGTGGTAGAGTG | 10 | 0.25 |
| GAP [GC] | TpG | | | |
| | Fw. | GGTTTTGTGTATGTTAGGTTTG | 11 | 0.75 |
| | Rev. | CCACATTACAACATAAACACAC | 12 | 0.75 |
| | Probe | TGTTGTGATGTTGGTTTTGGTGTAGAGGT | 13 | 0.125 |

Flow cytometry—For leukocyte purification, peripheral blood from healthy adult donors was fractionated by FCM into CD15$^+$, CD14$^+$, CD56$^+$ NK, CD19$^+$ B, CD4$^+$ and CD8$^+$ T cells with cell purities >97% and viability >99% as described previously (U. Baron, et al., DNA demethylation in the human FOXP3 locus discriminates regulatory T cells from activated FOXP3+ conventional T cells, *Eur. J. Immunol.* 37, 2378-2389 (2007)). For analytical cell quantification, absolute CD45$^+$ leukocyte counts were determined by a MACSQuant cytometer (Milteny Biotec, Bergisch Gladbach, Germany). Frequencies and absolute counts of CD15$^+$ neutrophils, CD19$^+$ B, CD56$^+$ NK, CD3+, CD4$^+$ and CD8$^+$ T cells and FOXP3$^+$ Tregs were calculated as previously described (U. Baron, et al., DNA demethylation in the human FOXP3 locus discriminates regulatory T cells from activated FOXP3+ conventional T cells, *Eur. J. Immunol.* 37, 2378-2389 (2007), A. Boldt, et al., Eight-color immunophenotyping of T-, B-, and NK-cell subpopulations for characterization of chronic immunodeficiencies, *Cytom. Part B—Clin. Cytom.* 86, 191-206 (2014)).

Statistical analysis—CP (crossing point) of triplicate measurements was computed by second-derivative maximum applying LC480 software (Roche, Mannheim, Germany) to yield copy numbers (plasmid units) by interpolating amplification (f) from calibration curves generated with serial dilutions of plasmid-based standards. Sample sizes for method comparison were chosen as 100 to provide 95% CI for limits of agreement at +/−0.34× the underlying standard deviation. Estimation of reference ranges demands a healthy population of at least 120 individuals for the nonparametric estimation of the 95% CI. The number of healthy cases was increased until exhaustion of available samples to accommodate for multidimensionality and estimation of extreme quantiles. Henze-Zinkler test was used to check for multivariate normality. Method comparison between flow cytometric and qPCR-based measuring technique was done as follows: Bivariate data from the two methods were illustrated in a scatterplot. Linear regression was performed testing a) for a slope different from 1 and b) an intercept different from 0. Bland-Altman plots were inspected analyzing bias and precision statistics (29). Acceptable precision was regarded as average deviation from the bias in percent. The limit of quantification for qPCR assays defined by the inter assay CV (0.2) was used as precision criterion and acceptable limits of agreement of 0.4. Wilcoxon-Rank-Sum Test was used to for median differences. The estimated bias, precision statistic and respective 95% CI are reported. For correlation, Pearson product-moment correlations were used. All p-values are two-sided. Statistics software R 3.3.0 was employed.

TABLE 1

Genetic defects and diagnostic classification by TREC/KREC and epigenetic qPCR for PID patients.

| | Disease Description | | | TREC/KREC Newborn Screening | | | Epigenetic qPCR Analysis | | | |
|---|---|---|---|---|---|---|---|---|---|---|
| | | | | | | | (CD3 G/D, GAPDH)[3] | (MVD, GAPDH)[3] | (LRP5, GAPDH)[3] | |
| Identifier | Classification | Gene Defect | Loss of Function Type | TREC[1] Positive [yes/no] | KREC[2] Positive [yes/no] | Screening Classification | Conspicious [yes/no] | Conspicious [yes/no] | Conspicious [yes/no] | Screening Classification |
| 1 | SCID | ADA | amorph | yes | yes | correctly identified | yes | yes | yes | correctly identified |
| 2 | SCID | ADA | amorph | no | yes | correctly identified | yes | yes | yes | correctly identified |
| 3 | DO-SCID[4] | ADA | hypomorph | no | yes | correctly identified | no | yes | yes | correctly identified |
| 4 | DO-SCID[4] | ADA | hypomorph | no | yes | correctly identified | yes | yes | yes | correctly identified |
| 5 | SCID | AK2 | amorph | yes | no | correctly identified | yes | yes | yes | correctly identified |
| 6 | SCID | AK2 | amorph | yes | yes | correctly identified | yes | yes | no | correctly identified |
| 7 | SCID | Artemis | amorph | yes | yes | correctly identified | yes | yes | yes | correctly identified |
| 8 | SCID | CD3D | amorph | yes | no | correctly identified | yes | yes | no | correctly identified |
| 9 | SCID w ME[5] | IL2RG | amorph | yes | no | correctly identified | no | no | no | not identified |
| 10 | SCID | IL2RG | amorph | yes | no | correctly identified | yes | yes | yes | correctly identified |
| 11 | SCID | IL7RA | amorph | yes | no | correctly identified | yes | no | no | correctly identified |
| 12 | SCID | IL7RA | amorph | yes | no | correctly identified | yes | yes | yes | correctly identified |
| 13 | SCID | IL7RA | amorph | yes | no | correctly identified | yes | yes | yes | correctly identified |
| 14 | DO-SCID[4] | JAK3 | hypomorph | no | no | not identified | yes | yes | yes | correctly identified |
| 15 | SCID | PNP | amorph | yes | yes | correctly identified | yes | yes | yes | correctly identified |
| 16 | SCID | PNP | amorph | yes | yes | correctly identified | yes | yes | yes | correctly identified |
| 17 | SCID | RAG1 | hypomorph | yes | yes | correctly identified | yes | yes | no | correctly identified |
| 18 | SCID | RAG1 | amorph | yes | yes | correctly identified | no | yes | yes | correctly identified |
| 19 | SCID | RAG2 | amorph | yes | yes | correctly identified | yes | no | yes | correctly identified |
| 20 | XLA | BTK | amorph | no | yes | correctly identified | yes | no | yes | correctly identified |
| 21 | XLA | BTK | amorph | no | yes | correctly identified | no | no | yes | correctly identified |
| 22 | XLA | BTK | amorph | no | yes | correctly identified | no | no | yes | correctly identified |
| 23 | XLA | BTK | amorph | no | yes | correctly identified | yes | yes | yes | correctly identified |
| 24 | XLA | BTK | hypomorph | no | no | not identified | no | yes | yes | correctly identified |

[1] TREC values ≤6 copies per dot were considered positive;
[2] KREC values ≤4 copies per dot were considered positive;
[3] Values outside the joint 99% reference range were considered conspicious, see FIG. 5;
[4] Delayed onset SCID;
[5] SCID with maternal engraftment

TABLE 2

Stability testing of DBS. T cell subpopulations measured by epigenetic qPCR analysis from blood, spotted, dried on Guthrie cards and stored for various times and at different temperatures.

| | Storage condition | CD3+ T cells Mean [%] | Standard Deviation [%] | CD4+ T cells Mean [%] | Standard Deviation [%] | CD8+ T cells Mean [%] | Standard Deviation [%] |
|---|---|---|---|---|---|---|---|
| 1 day | 4° C. | 20.94 | 0.62 | 18.85 | 0.36 | 5.73 | 0.51 |
| | Room temperature | 21.19 | 1.07 | 17.87 | 2.39 | 5.22 | 0.13 |
| | 37° C. | 24.36 | 1.64 | 22.21 | 4.29 | 5.94 | 0.64 |
| 1 week | 4° C. | 27.46 | 3.88 | 21.11 | 1.28 | 7.14 | 2.24 |
| | Room temperature | 24.21 | 0.50 | 23.87 | 2.50 | 7.39 | 0.75 |
| | 37° C. | 24.41 | 2.32 | 21.42 | 0.86 | 7.14 | 0.26 |
| 6 weeks | 4° C. | 21.56 | 3.38 | 22.78 | 5.26 | 6.19 | 0.80 |
| | Room temperature | 24.09 | 3.44 | 19.76 | 6.24 | 7.62 | 2.54 |
| | 37° C. | 22.91 | 1.42 | 21.34 | 1.23 | 5.98 | 0.39 |

TABLE 6

Epigenetic qPCR from DBS spotted with diluted blood. The three main T cell sub-populations were measured by epigenetic qPCR in different concentrations from a dilution series of EDTA-blood samples.

| | | CD3+ T cells Mean [%] | Standard Deviation [%] | CD4+ T cells Mean [%] | Standard Deviation [%] | CD8+ T cells Mean [%] | Standard Deviation [%] |
|---|---|---|---|---|---|---|---|
| Donor A | undiluted | 22.46 | 0.00 | 15.20 | 0.00 | 8.43 | 0.00 |
| | 1:3 dilution | 19.89 | −11.42 | 12.01 | −20.97 | 5.84 | −30.80 |
| | 1:9 dilution | 19.49 | −13.22 | 16.45 | 8.21 | 7.26 | −13.97 |
| | 1:27 dilution | 15.90 | −29.21 | NA | NA | NA | NA |
| Donor B | undiluted | 19.39 | 0.00 | 20.92 | 0.00 | 5.70 | 0.00 |
| | 1:3 dilution | 17.27 | −10.96 | 17.60 | −15.88 | 4.03 | −29.31 |
| | 1:9 dilution | 18.64 | −3.90 | 21.60 | 3.22 | 5.39 | −5.46 |
| | 1:27 dilution | 15.88 | −18.08 | 23.10 | 10.41 | NA | NA |
| Donor C | undiluted | 12.40 | 0.00 | 10.86 | 0.00 | 4.09 | 0.00 |
| | 1:3 dilution | 12.45 | 0.45 | 11.18 | 2.89 | 3.29 | −19.59 |
| | 1:9 dilution | 8.61 | −30.57 | 10.45 | −3.76 | 5.50 | 34.33 |
| | 1:27 dilution | 23.11 | 86.42 | NA | NA | NA | NA |

The invention claimed is:

1. A method for producing and detecting a panel of amplicons from a human subject having immunodysregulation polyendocrinopathy enteropathy X-linked (IPEX) or IPEX-like disease, the method comprising:
   a) bisulfite treating isolated genomic DNA from a cell sample of a human subject to convert unmethylated cytosines into uracils;
   b) producing the panel of amplicons by:
      i) amplifying from the bisulfite treated DNA a human gene region for FOXP3, a human CD4 gene region, a human CD3 gene region, and a housekeeping gene region; and
      ii) amplifying a nucleic acid template comprising unconverted glyceraldehyde 3-phosphate dehydrogenase (GAPDH) artificial region with inverted CpG dinucleotides (GAP[GC]), and
   c) detecting the panel of amplicons.

2. The method according to claim 1, further comprising the step of analyzing a methylation status of at least one CpG position in the human gene region for FOXP3.

3. The method according to claim 1, further comprising determining the amount of T cells in said sample based on the number of amplicons in the panel.

4. The method according to claim 1, wherein the panel of amplicons comprises an amplicon from the Treg-specific demethylated region (TSDR) in FOXP3.

5. The method according to claim 1, further comprising analyzing the panel of amplicons using a method selected from a methylation specific enzymatic digest, bisulfite sequencing, promoter methylation analysis, CpG island methylation analysis, MSP, HeavyMethyl, MethyLight, and Ms-SNuPE.

6. The method according to claim 1, further comprising a mutational analysis step of the FOXP3 gene region.

7. The method according to claim 1, wherein said sample is selected from a fresh blood sample, a peripheral or capillary blood sample, a sample of blood lymphocytes or a fraction thereof, a tissue sample, a previously frozen blood or tissue sample, and a dried blood sample.

8. The method according to claim 1, wherein said human subject is selected from a fetus, a newborn, and a child.

9. A method of treating IPEX syndrome and/or IPEX-like syndrome in a human subject, the method comprising:
   producing and detecting a panel of amplicons by a method comprising:
      a) bisulfite treating isolated genomic DNA from a cell sample of a human subject to convert unmethylated cytosines into uracils;
      b) producing the panel of amplicons by amplifying from the bisulfite treated DNA a human gene region for FOXP3, a human CD4 gene region, a human CD3 gene region, and a housekeeping gene region; and
      c) detecting the panel of amplicons, and
   treating IPEX syndrome when the amplicons for the human gene region for FOXP3 show demethylation of at least one CpG position above 99%, or
   treating IPEX-like syndrome when the amplicons for the human gene region for FOXP3 show demethylation of at least one CpG position between 95% and 99%.

10. The method of claim 3, wherein the amplifying is performed with qPCR, and the method further comprises determining the number of amplicons per cell type in the panel.

11. The method of claim 1, wherein the housekeeping gene comprises beta-2microglobulin (B2M), peptidylprolyl isomerase A (PPIA), eukaryotic translation elongation factor 1 gamma (EEFI G), succinate dehydrogenase complex subunit A (SDHA), glyceraldehyde 3-phosphate dehydrogenase (GAPDH), hydroxymethyl-bilane synthase (HMBS), TATA box-binding protein (TBP), 18s Ribosomal RNA (18sRNA), phosphoglycerate kinase 1 (PGK1), or beta-actin (BACT).

12. The method of claim 1, wherein the amplifying uses primer pairs comprising SEQ ID NOs: 1 and 2, 3 and 4, 8 and 9, and 11 and 12.

13. The method of claim 1, wherein the amplifying uses probes comprising SEQ ID NOs: 5, 6, 10, and 13.

14. The method of claim 1, wherein the amplifying uses primer pairs comprising SEQ ID NOs: 1 and 2, 3 and 4, and 11 and 12, and probes comprising SEQ ID NOs: 5, 6, and 13.

15. The method of claim 2, wherein the methylation status of the at least one CpG position in the human gene region for FOXP3 is between 95% and 99% demethylated.

16. The method of claim 2, wherein the methylation status of the at least one CpG position in the human gene region for FOXP3 is greater than 99% demethylated.

* * * * *